United States Patent [19]

Narayanan

[11] Patent Number: 5,389,688
[45] Date of Patent: Feb. 14, 1995

[54] WATER BASED MICROEMULSION FORMULATIONS

[75] Inventor: Kolazi S. Narayanan, Palisades Park, N.J.

[73] Assignee: Isp Investments Inc., Wilmington, Del.

[21] Appl. No.: 40,239

[22] Filed: Mar. 30, 1993

Related U.S. Application Data

[63] Continuation-in-part of Ser. No. 964,245, Oct. 21, 1992, abandoned, which is a continuation of Ser. No. 654,250, Feb. 12, 1991, abandoned, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^6$ ............................................. A01N 25/00
[52] U.S. Cl. ..................... 514/788; 514/937; 514/938
[58] Field of Search ................. 514/778, 937, 938; 504/116

Primary Examiner—Marianne M. Cintins
Assistant Examiner—Kevin E. Weddington
Attorney, Agent, or Firm—Walter Katz; Marilyn J. Maue; Joshua J. Ward

[57] ABSTRACT

A highly stable composition composed of a water insoluble agriculturally active ingredient, a surfactant, a lactam having the formula:

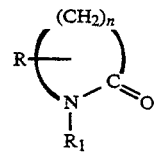

wherein
R is hydrogen or branched or straight chained alkyl having from 1 to 16 carbon atoms and $R_1$ is branched or straight chained alkyl having from 1 to 16 carbon atoms, with the provision that the sum of the carbon atoms in R and $R_1$ is less than or equal to 16; and n is 3, 4, or 5;

and at least about 80 percent by weight water, and wherein the specific agriculturally active ingredient, surfactant, and lactam and amounts of each are such that composition is in the form of a microemulsion.

11 Claims, No Drawings

WATER BASED MICROEMULSION FORMULATIONS

CROSS REFERENCE TO RELATED APPLICATION

This application is a continuation-in-part of application Ser. No. 07/964,245, filed Oct. 21, 1992, now abandoned which is a continuation of application, Ser. No. 07/654,250, filed Feb. 12, 1991, now abandoned which, in turn, is a continuation-in-part of Ser. No. 07/546,014, filed June 28, 1990, now U.S. Pat. No. 5,156,666, which in turn, is a continuation-in-part of application Ser. No. 07/505,030, filed Apr. 5, 1990, now U.S. Pat. No. 5,160,528, which, in turn, is a continuation-in-part of application Ser. No. 07/448,707, filed Dec. 11, 1989, now U.S. Pat. No. 5,071,463, (hereinafter, collectively referred to as the Parent Applications) the contents of all of which are incorporated herein by reference.

BACKGROUND OF THE INVENTION

I. Field of the Invention

The invention relates to a delivery system for agriculturally active chemicals. More particularly, the invention relates to a microemulsion of a difficult to dissolve agricultural chemical and concentrates for producing such microemulsions.

DEFINITIONS

As used herein, the following terms have the meanings indicated:
(a) "macroemulsion" means an emulsion of water in oil or oil in water wherein the interior phase is in the form of visually discernable droplets and the overall emulsion is cloudy, and wherein the droplet diameter is greater than about 100 millimicrons.
(b) "microemulsion" means an oil in water or water in oil, transparent thermodynamically stable dispersion of two or more immiscible liquids wherein the dispersed phase consists of small droplets with diameters in the range of about 10 to 100 millimicrons. Such microemulsions are clear and contain at least about 80% by weight water.
(c) "clear" or "transparent" as applied to a microemulsion means that the composition appears as a single phase without any particulate or colloidal material or a second phase being present when viewed by the naked eye.
(d) "substantially insoluble" or "insoluble" means that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.
(d) High degree of loading in the concentrate means an agriculturally active ingredient content of at least about 5 percent by weight.
(e) the term "agriculturally active chemical or ingredient" (AAC) means compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests.

II. Description of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

An attempt to provide concentrates of agriculturally useful chemicals for producing macroemulsions is disclosed in South African Patent Application No. 695,393, filed Jul. 25, 1969. This application is directed to the formulation of a concentrate substantially water-insoluble pesticides for agricultural use. The pesticides, either in oil or solid form, are mixed with pyrrolidones having a hydrogen or a lower alkyl group containing from 1 to 4 carbon atoms attached to the nitrogen atom of the pyrrolidone ring. The application discloses that concentrated solutions of difficult to dissolve pesticides could be formulated and that such concentrates exhibited good stability. The concentrates utilized are those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

This prior art does not offer a solution to the problem arising from the difficulty in maintaining the stability of the emulsion after the concentrate is diluted with water. Consequently, unless the diluted form of the concentrate is used immediately after emulsification, it is difficult to provide a stable diluted formulation for application to the plants, soil, pests, and the like.

U.S. Pat. No. 4,798,837 discloses an emulsifiable concentrate of the pesticidal compound (CGA):

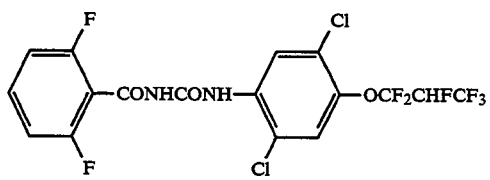

This active concentrate contains 10% of the active ingredient using 30% cyclohexanone as the solvent. However, cyclohexanone is highly toxic. For such agricultural uses, it is desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate.

In addition, for such agricultural uses, it is desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate. Moreover, many organic solvents which have been used in the past, even those exhibiting relatively low toxicities, are not biodegradable and thus remain as a pollutant.

The Parent Applications referred to hereinabove have provided solutions to the problem of providing stable macroemulsions of insoluble agricultural chemicals in aqueous systems. This is accomplished by the use of long and short chain alkyl lactams for formation of emulsifiable concentrates of agricultural chemicals. Also see U.S. patent application Ser. No. 257,596, filed Oct. 14, 1988, the contents of which are incorporated herein by reference, which discloses the use of long chain alkyl lactams to prepare emulsifiable concentrates of agriculturally active ingredients, e.g., herbicides, fungicides, pesticides, and the like, which on dilution with water, form stable macroemulsions.

While these patent applications disclose the preparation of emulsions of a wide variety of agriculturally active chemicals which are normally highly insoluble in water, the emulsions produced from all of these prior art concentrates are macroemulsions. The macroemulsions which result from their dilution with water, while relatively stable, may, at some point in time, settle out into two phases or more.

It is desirable, however, to provide compositions which will deliver effective amounts of insoluble agriculturally active compound which exhibit improved stability with respect to the emulsion. In addition, it is desired to provide increased chemical stability for such agricultural compounds. Thus, certain agricultural compounds, notably, insecticides, are relatively chemically unstable in water and tend to hydrolyze after a short period of time. As a result, even short periods of increased chemical stability for such compounds are advantageous.

It is also desirable to increase the efficacy of a given agricultural compound relative to its loading content. It has been theorized that microemulsions can improve the efficacy of agriculturally active compounds relative to equivalent levels of the same compound in a macroemulsion composition. See Skelton, P. R., Munk, B. H., and Collins, H. M., "Formulation of Pesticide Microemulsions", *Pesticide Formulations and Application Systems; 8th Volume, ASTM STP 980*, D. A. Hovde and G. B. Beestman, Eds., kmerican Society for Testing and Materials, Philadelphia, 1988. See also U.S. Pat. No. 3,954,967, and Canadian Patent 1025687. For a discussion of Microemulsions, see *Microemulsions, Theory and Practice*, Leon M. Prince, Academic Press, 1977 and Microemulsions-Properties Novel Chemistry BH Robinson, Chemistry in Britain 26 (1990), page 342.

SUMMARY OF THE INVENTION

We have discovered a novel microemulsion which can be used to place highly water insoluble agriculturally active compounds in a state, which is essentially equivalent to a dissolved state, which microemulsions exhibit prolonged stability.

More particularly, we have discovered a highly stable composition composed of a water insoluble agriculturally active ingredient, a surfactant, a lactam having the formula:

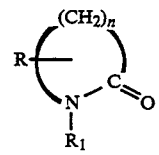

wherein
R is hydrogen or branched or straight chained alkyl having from 1 to 16 carbon atoms and $R_1$ is branched or straight chained alkyl having from 1 to 16 carbon atoms, with the provision that the sum of the carbon atoms in R and $R_1$ is less than or equal to 16; and n is 3, 4, or 5;

and at least about 80 percent by weight water, and wherein the specific agriculturally active ingredient, surfactant, and lactam and amounts of each are such that composition is in the form of a microemulsion.

Of importance with the microemulsions of the present invention is the fact that even though they contain large amounts of water, they exhibit a long shelf life in the microemulsion form. This is of special advantage for consumer end uses, e.g., household uses, domestic pest control, and those end uses wherein dilution of a concentrate at the site is unfeasable or undesirable. In addition, the inventive compositions do not contain any materials which are disadvantages from an environmental point of view, e.g., toxic solvents and the like.

DETAILED DESCRIPTION OF THE INVENTION

AAC's normally take the form of water-immiscible or oily liquids and/or solids. Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

| | |
|---|---|
| cyclocompounds: | 6,7,8,9,10,10-hexachloro- |

| | |
|---|---|
| | 1,5,5a,6,9,9a-hexahydro-6,9-methano-2,4,3-benzodioxathiepin-3-oxide |
| carbamates: | 2-isopropyl phenyl-N-methyl carbamate;<br>2-(1,3-dioxolan-2yl) phenylmethyl carbamate;<br>2,3-isopropylidine dioxyphenyl methyl carbamate; |
| Carbaryl: | 1-naphthyl-N-methylcarbamate |
| animal and plant derivatives: | chlorinated hydrocarbons derived from Southern pine; naturally occuring lactone glycoside; |
| synthetic pyrethroids: | (±) α-cyano-3-phenoxybenzyl (±) cis, trans 3-(2,2-dichlorovinyl)-2,2-dimethyl cyclopropane carboxylate;<br>(RS)-3-allyl-2-methyl-4-oxocyclopent-2-enyl (1RS)-cis,trans-chrysanthemate;<br>3-phenoxybenzyl (1RS)-cis,trans-3-(2,d-dichlorovinyl)-2,2-dimethylcyclopropanecarboxylate;<br>3,4,5,6-tetrahydrophthalimidomethyl (±)-cis,trans-chrysanthemate);<br>5-[2-(2-*butoxyethoxy)ethoxymethyl]-6-propyl-1,3-benzodioxole;<br>(RS)-α-cyano-3-phenoxybenzyl 2,2,3,3-tetramethylcyclopropanecarboxylate;<br>(±) cyano (3-phenoxyphenyl methyl (±)-4-(difluoromethyoxy) α-(1-methylethyl) benzene acetate; |
| phenoxy compounds and non-phosphate: | 2,2-bis(p-methoxy phenyl)-1,1,1,trichloroethane;<br>1,3,5,tri-n-propyl-1,3,5-triazine-2,4,6 (1H,3H,5H) trione;<br>ethyl (2E, 4E)-3,7,11-trimethyl-2,4-dodeca dienoate;<br>1-[4-)2-chloro-α,α,α-trifluoro-p-tolyloxy)-2-fluorophenyl]-3-(2,6-difluorobenzoyl)urea;<br>1-decyloxy 4-[(7-oxa-oct-4-ynyl)]-oxybenzene; |
| organic phosphates: | dimethyl phophate ester of 3-hydroxy-N,N-dimethyl-cis-crotonamide;<br>2-chloro-1-(2,4-dichloro phenyl) vinyl diethylphosphate;<br>4-(methyl thio) phenyl dipropyl phosphate; |
| thiophosphates: | 0,0-diethyl-0-4-nitrophenyl phosphorothioate;<br>0,0-diethyl-0-(2,isopropyl-6-methyl-5-pyrimidinyl) phosphorothioate;<br>2-diethylamino-6-methyl pyrimidine-4-yl dimethyl phosphorothioate; |
| dithiophosphates and others: | 0,0-dimethyl phosphorodithioate ester of diethylmercapto succinate;<br>0-ethyl-S-phenyl ethyl phosphorodithioate;<br>5,5-dimethylperhydropyrlmidin-2-one 4-trifluoromethyl-α-(4-trifluoromethylstyryl)-cinnamylidenehydrazone (hydrmethylnon). |

*this compound is a known synergist for synthetic pyrethroids

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g., triazines, pyridines, pyridazones, picolinic acid, and urea derivates and phosphates. (See *Agricultural Chemicals*, Book II, *Herbicides*, 1986–87 Edition, W. T. Thomson, Thomson Publications, Fresno, Calif. 93791.) Exemplary of the above compounds are:

| | |
|---|---|
| phenoxy compounds: | 2,4-Dichlorophenoxy acetic acid<br>2,4,5-trichloro phenoxyacetic acid;<br>4-(2,4-dichlorophenoxy) butyric acid;<br>S-ethyl 2 methyl-4-chlorophenoxy-thioacetate;<br>2-methyl-4-chloro-phenoxy acetic acid;<br>methyl 5-(2,4-dichloro-phenoxy)-2-nitrobenzoate; |
| benzoic and acetic acids of phthalic compounds: | 3,6-dichloro-o-anisic acid<br>4-chloro-2-oxo benzothiazolin-3-yl acetic acid;<br>N-1-Naphthyl-phthalamic acid; |
| nitriles and aniline derivatives: | 3-5-dibromo-4-hydroxybenzonitrile;<br>α,α,α,trifluoro-2,6-dinitro-N,N-dipropyl-p-tolinidine;<br>N-(1-ethylpropyl)-2,6-dinitro-3,4-xylidine; |
| amides, acetamides, anilides: | N,N-diethyl-2-(1-naphthalenyl oxy)-propionamide;<br>2,6-dimethyl-N-2' methoxy-ethyl-chloro-acetanilide;<br>3',4'-dichloro-propionanilide;<br>α-chloracetic-N-(3,5,5-trimethyl-cyclohexen-1-yl)-N-isopropylamide;<br>4-benzyl-N-isopropyl trimethyl acetamide; |
| thiocarbamates: | S-Ethyl dipropyl thiocarbamate; |
| urea derivatives: | 3-(5-tert-butyl-3-isoxazoyl)-1,1-dimethyl urea;<br>N-(2,6-trifluoro-benzoyl)-N'-[2,5-dichloro-4-(1,1,2,3,3,3-hexafluoropropyloxy) phenyl] urea; |
| pyrrolidone derivatives: | 1-(m-trifluoro methyl phenyl)-3-chloro-4-chloromethyl-2-pyrrolidone; |
| amino acid derivatives: | methyl N-benzoyl-N-(3-chloro-4-fluorophenyl)-DL alarinate;<br>N-chloroacetyl-N-(2,6-diethyl phenyl)-glycine ethyl ester; |
| carbamates: | Isopropyl-m-chlorocarbanilate;<br>3-Ethoxy (carbonyl aminophenyl)-N-phenyl carbamate; |
| heterocyclics: | 4-amino-3,5-dichloro-6-fluoro-2-pyridyloxy acetic acid;<br>4-(1,2-Dimethyl-N-propyl amino)-2-ethyl amino-6-methyl thio-S-triazine;<br>2-[4,5-dihydro 4-methyl-4-(1-methyl ethyl)-5-oxo-1 H-imidazoyl-2yl-3-byridinecarboxylic acid;<br>2-[3,5-dichlorophenyl)-2-(2,2,2-trichloroethyl) oxinane;<br>Butyl-9-hydro-fluorene-(9)-carboxylate;<br>2-[1-(ethoxy imino) butyl]-3-hydroxy-5-(2H-tetra hydro thio-pyran-3-yl)-2-cyclohexene-ione;<br>2-(2 chlorophenyl) methyl-4,4-dimethyl-3-iso oxazolidinone; |
| phosphates: | 0-ethyl-0-(3-methyl-6-nitro phenyl) N-sec-butyl phosphoro thio amidate. |

Typical fungicides include (See *Agricultural Chemicals*, Book IV, *Fungicides*, 1989 Revision, W. T. Thomson, Thomson Publications, Fresno, Calif. 93791):

| | |
|---|---|
| organic compounds: | 2,5-dimethyl-N-Cyclohexyl-N-methoxy-3-furan carboxamide;<br>5-Ethyoxy-3-trichloromethyl-1,2,4-thiadiazole; |

| | -continued |
|---|---|
| | 3-(2-methyl piperidino) propyl 3,4-dichlorobenzoate; |
| | N,N'-(1,4-piperazinediyl bis (2,2,2-trichloro) ethylidene) bis formamide; |
| | Tetramethyl thiuram disulfide; |
| | O-Ethyl-S,S,diphenyl-dithiophosphate; |
| | 5,10-dihydro-5,10-dioxo naphtho (2,3,9)-p-dithiin-2,3-dicarbonitrile; |
| | 2-(Thiocyano methyl thio) benzothiazole; |
| | α-2-(4-chlorophenyl) ethyl]-α-(1,1-dimethyl ethyl)-1 H-1,2,4-triazole-1-ethanol; |
| morpholines: | N-tridecyl-2,6-dimethyl morpholine; |
| | 4-N-dodecyl-2,6-dimethyl morpholine; |

Typical fumigants, growth regulators, repellants, and rodenticides include (See *Agricultural Chemicals*, Book III, *Fumigants*, 1988–1989 Revision, W. T. Thomson, Thomson Publications, Fresno, Calif. 93791):

| | |
|---|---|
| growth regulants: | 1,2 Dihydro-6-ethyoxy-2,2,4-trimethylquinoline; |
| | (2-chloroethyl) phosphoric acid; |
| | 4-[acetamino) methyl]-2-chloro-N (2,6-diethyl phenyl acetamide; |
| | Benzoic acid, 3,6 dichloro-2-methoxy,2-ethoxy-1-methyl-2-oxo ethyl ester; |
| repellants: | 0,0-dimethyl-0-((4-methyl thio[-m-tolyl] phosphorothioate; |
| | Tetriary butyl-sulfenyl dimethyl dithio carbamate; |
| seed softener: | 2-chloro-6-(trichlomethyl) pyridine; |
| | 5-ethoxy-3-trichloromethyl-1,2,4-thiadiazole; |
| | N-phenyl-N'-1,2,3-thiadiazol-5-yl urea; |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro-1H-azepine-1-carbothioate,
PP 511 0,0-dimethyl-(2-diethylamine 4-methyl-6-pyrimidinyl) carbamate,
PP 211 0,0-diethyl O-(2-diethylamine-4-methyl-6-pyrimidinyl) phosphorocarbamate,
Chlordane
5-Ethoxy-3-(trichlorometyl)-1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamate (RO-NEET®),
Malathion (S-(1,2 -dicarboxyethyl)-0,0-dimethyl phosphorodithioate),
Diazinon (0,0-diethyl,0-(2-isopropyl-4-methyl-6-pyrimidinyl) phosphorothioate,
O-Ethyl-S-phenyl-ethylphosphonodithioate (DYFONATE®), Toxaphene (Octachlorocamphene),
Bromoxynil (3,5-dibromo-4-hydroxy benzonitrile ester of n. octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-trriazine)
Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s-(o,o dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2,-Bis(p-methoxyphenyl)-1,1-trichloroethane PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methyl-pyrimidine*
* Manufactured by Imperial Chemical Industries Limited
C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl)-N-methylurea
NIA 11092 1,1-dimethyl-3-[3-(n-t-butyl carbamyloxy)-phenyl]urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoyl)-2-benzimidazol carbamic acid, methyl ester (BENLATE ®)]

Preferred lactams suitable for use in the invention are alkyl pyrrolidones having the formula:

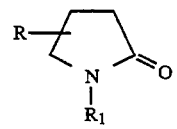

wherein R is hydrogen or linear or branched alkyl having from 1 to 16 carbon atoms and $R_1$ is linear or branched alkyl having from 1 to 16 carbon atoms, with the provision that the sum of number of carbon atoms in R and $R_1$ must be less than or equal to 16.

Preferred lactams are those wherein R is hydrogen and $R_1$ is methyl, ethyl, butyl, octyl, or iso-octyl. Of these, particularly preferred are N-methyl pyrrolidone, N-octyl pyrrolidone, and N-isooctylpyrrolidone.

The method of preparing the inventive composition involves merely add mixing the ingredients. Normally, it is best to first add the agriculturally active compound to the lactam component and then admix the surfactant. The water is normally added after the first three ingredients are mixed. However, there is no particular criticality to the sequence of addition and mixing.

Surfactant suitable for use in the inventive composition include ethoxylated alkyl phenols, linear aliphatic polyesters, linear aromatic polyesters, polyalkenyloxyalcohol, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfates, sulfonates, and their salts, salts of sulfated nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of non-ionic surfactants of the ethylene oxide type which are mixtures of diesters of phosphoric acid. (See, for example, McCutcheon's, *Emulsifiers and Detergents* (1989), published by McCutcheon's Division of M.C. Publishing Co., Glen Rock, N.J.)

The specific components as well as their amounts in the inventive composition may be revised over a wide range within the definitions given above, and are limited only in that the final product, upon dilution, must form the inventive microemulsion.

The AAC concentration in the microemulsion concentrate should be as high as possible so long as the AAC does not precipitate upon dilution of the concentrate with at least 80% weight water, preferably 90% water, and, most preferably, 95-99% water, for a reasonable period of time. Precipitation (crystal formation) of the AAC on standing not only depletes the amount of AAC in solution, it can also lead to fouling of application equipment, i.e., sprayers, etc.

With the present invention, it is possible to obtain microemulsion concentrates with suitable AAC concentrations in excess of 0.5 weight percent, preferably in excess of 5%, and, most preferably, in excess of 10%, which form a stable, transparent microemulsion upon being diluted with water. Depending on the particular AAC, the concentration of the AAC in the concentrate suitably ranges from about 0.5 to 25% based on the total weight of the composition before dilution.

Suitably, the amount of surfactant in the microemulsion concentrate is from about 0.2 to 80%, preferably 5–60%, and, most preferably 10–50%, based on the total weight of the composition. Normally, the amount of surfactant used will depend on the amount of AAC. A suitable ratio of AAC to surfactant in the microemulsion concentrate is from about 1:0.3 to 1:10, preferably 1:0.5 to 1:8, and, most preferably, 1:1–1:6.

The final use concentration of the AAC, i.e., after dilution to form the aqueous microemulsion, depends on the particular AAC. However, it is important that, upon dilution, the diluted form remain stable for a time period sufficient to allow it to be applied. This, of course, will vary with the schedule for the application in the field or end user. A suitable aqueous microemulsion composition in accordance with the invention comprises about 0.005 to 2 weight percent, preferably 0.01 to 0.5%, of the AAC; about 0.01 to 15 weight percent of the lactam, preferably 0.03 to 10%; about 0.01 to 15 weight percent of the surfactant(s), preferably 0.03 to 5%; and the remainder is water.

With the inventive aqueous microemulsion, prolonged stability is obtained, and formulations are present in a ready-to-use format for consumer use. Conventional adjuvants also may be added to the inventive composition, e.g., film forming polymers, i.e., polyvinylpyrrolidone, viscosity modifiers, and the like, so long as they do not destroy or adversely affect the microemulsive state.

The following examples illustrate the present invention*:

* In the examples, all compositional percentages are percent by weight of the total composition unless otherwise indicated.

Experimental Procedure

A. Formulations:

Formulations were prepared by weighing and mixing the exact proportions of the ingredients. Typically 100 g samples of the water-based formulations were prepared for each evaluation in 4 oz. stoppered bottles. When a lactam was used, the AAC was dissolved completely in the measured quantity of the lactam. The surfactant(s) was added to the AAC or to the solution of the AAC in the lactam (if a lactam was used). The contents were mixed in an automatic orbital shaker until the AAC dissolved completely or the mixture became homogeneous. Normally, this took about thirty minutes. A concentrate was then obtained which was either diluted immediately or stored. In those instances where the concentrate was stored for a period of time from 4 hours to two weeks and then diluted with water, this fact is indicated in the tabular results, e.g., Table 5.

The water-based microemulsions were prepared by adding the required quantity of the concentrate to water. The dilution water was either deionized water or World Health organization (WHO) standard hard water of hardness of 342 ppm expressed as $CaCO_3$ equivalent.

B. Evaluation of Stability

The samples were visually examined for clarity, precipitation, and separation or turbidity at ambient temperatures. Stable formulations were observed for as long as six months. The formulations were considered stable if they remained clear by visual observation for more than 4 days. Formulations that became cloudy or separated within 24 hours were considered unstable.

However, certain AAC's are known to be unstable under certain conditions, for example, they may hydrolyze in water, e.g., Hydramethylnon, Carbaryl, and the like. Accordingly, stability of the microemulsion for such an AAC must be judged using a different standard from AAC's which are not subject to such chemical instability. Generally, for such a compound, stability of four hours is considered satisfactory since the diluted material would as a practical matter have to be used shortly after dilution. In these instances, we have found indications that the inventive microemulsion increase the chemical stability of the AAC.

Promising formulations were evaluated for stability at lower and higher temperatures in the range from 10° C. through 45° C. Samples were stored at fixed temperatures of 10° C. through 45° C. and were observed visually as a function of time.

In a few cases, the clarity was also measured instrumentally and expressed as NTU (Nephelometric turbidity units) using a Hach Ratio Turbidimeter. Samples with values ≦50 NTU were considered visually clear.

In the following tables, the last recorded visual observation represents the last time period that a visual observation was made, e.g., if the last observation shown is for the two week period, no further observations were made for that run. Also, in those runs indicating a hiatus between two identical observations, interim observations were the same as those indicated before and after the hiatus, e.g., for Run No. 1, the sample was "cloudy" for 1 day, 2 days, and 4 days; and for Run No. 6, the sample was clear for 1 day, 2 days, and 4 days.

TABLE 1

Microemulsion Composition for D-Allethrin (Percent by weight) and Stability

| Run No. | 1 | 2 | 3 | 4 | 5 |
|---|---|---|---|---|---|
| Active Ingredient(s): | | | | | |
| D-Allethrin | 0.05 | 0.05 | 0.05 | 0.05 | 0.05 |
| Tetramethrin | 0 | 0 | 0 | 0 | 0 |
| Permethrine | 0 | 0 | 0 | 0 | 0 |
| Piperonyl Butoxide | 0 | 0 | 0 | 0 | 0 |
| Lactam(s): | | | | | |
| N-Methylpyrrolidone | 0.45 | 0.45 | 0.45 | 0.45 | 0.45 |
| N-Octylpyrrolidone | 0.1 | 0.3 | 0.6 | 0 | 0 |
| Surfactant(s): | | | | | |
| Igepal CO 630 | 0 | 0 | 0 | 0 | 0 |
| Gafac RE 610 | 0 | 0 | 0 | 0.1 | 0.3 |
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0 | 0 | 0 | 0.1 | 0.3 |
| Stability: | | | | | |
| Time, observation at ambient conditions | | | | | |
| 0 time | cloudy | cloudy | cloudy | cloudy | sl hazy |
| 1 day | | | | | |
| 2 days | | | | | |
| 4 days | | | | | |
| 1 week | cloudy | cloudy | cloudy | hazy | sl hazy |
| 2 weeks | | cloudy | cloudy | cloudy | clear |
| 4 weeks | | | | | |
| 6 weeks | | | | | |
| 2 months | | | | | |
| 4 months | | | | | |
| 6 months | | | | | |

| Run No. | 6 | 7 | 8 | 9 | 10 |
|---|---|---|---|---|---|
| Active Ingredient(s): | | | | | |
| D-Allethrin | 0.05 | 0.05 | 0.05 | 0.05 | 0.05 |
| Tetramethrin | 0 | 0 | 0 | 0 | 0 |
| Permethrine | 0 | 0 | 0 | 0 | 0 |
| Piperonyl Butoxide | 0 | 0 | 0 | 0 | 0 |
| Lactam(s): | | | | | |
| N-Methylpyrrolidone | 0.45 | 0.45 | 0.45 | 0.45 | 0.45 |
| N-Octylpyrrolidone | 0 | 0 | 0 | 0 | 0 |
| Surfactant(s): | | | | | |
| Igepal CO 630 | 0 | 0.1 | 0.3 | 0.6 | 0.2 |
| Gafac RE 610 | 0.6 | 0 | 0 | 0 | 0 |

TABLE 1-continued

Microemulsion Composition for D-Allethrin (Percent by weight) and Stability

| | | | | | |
|---|---|---|---|---|---|
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0.6 | 0.1 | 0.3 | 0.6 | 0.2 |
| Stability: | | | | | |
| Time, observation at ambient conditions | | | | | |
| 0 time | clear | hazy | clear | clear | clear |
| 1 day | | | | | |
| 2 days | | | | | |
| 4 days | | | | | clear |
| 1 week | clear | cloudy | clear | clear | clear |
| 2 weeks | clear | cloudy | clear | clear | clear |
| 4 weeks | | | | | |
| 6 weeks | | | | | |
| 2 months | | | | | |
| 4 months | | | | | |
| 6 months | | | | | |

| Run No. | 11 | 12 | 13 | 14 | 15 |
|---|---|---|---|---|---|
| Active Ingredient(s): | | | | | |
| D-Allethrin | 0.05 | 0.05 | 0.05 | 0.05 | 0.05 |
| Tetramethrin | 0 | 0 | 0 | 0 | 0 |
| Permethrine | 0 | 0 | 0 | 0 | 0 |
| Piperonyl Butoxide | 0 | 0 | 0 | 0 | 0 |
| Lactam(s): | | | | | |
| N-Methylpyrrolidone | 0.45 | 0.45 | 0.45 | 0.45 | 0.45 |
| N-Octylpyrrolidone | 0 | 0 | 0.05 | 0.15 | 0.3 |
| Surfactant(s): | | | | | |
| Igepal CO 630 | 0.4 | 0.5 | 0 | 0 | 0 |
| Gafac RE 610 | 0 | 0 | 0.05 | 0.15 | 0.3 |
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0.4 | 0.5 | 0.05 | 0.15 | 0.3 |
| Stability: | | | | | |
| Time, observation at ambient conditions | | | | | |
| 0 time | clear | clear | cloudy | hazy | clear |
| 1 day | | | | | |
| 2 days | | | | | |
| 4 days | clear | clear | cloudy | clear | clear |
| 1 week | clear | clear | cloudy | clear | clear |
| 2 weeks | clear | clear | | | |
| 4 weeks | | | | | |
| 6 weeks | | | | | |
| 2 months | | | | | |
| 4 months | | | | | |
| 6 months | | | | | |

| Run No. | 16 | 17 | 18 | 19 | 20 |
|---|---|---|---|---|---|
| Active Ingredient(s): | | | | | |
| D-Allethrin | 0.05 | 0.05 | 0.05 | 0.05 | 0.05 |
| Tetramethrin | 0 | 0 | 0 | 0 | 0 |
| Permethrine | 0 | 0 | 0 | 0 | 0 |
| Piperonyl Butoxide | 0 | 0 | 0 | 0 | 0 |
| Lactam(s): | | | | | |
| N-Methylpyrrolidone | 0.45 | 0.45 | 0.45 | 0.45 | 0.45 |
| N-Octylpyrrolidone | 0.05 | 0.15 | 0.3 | 0 | 0 |
| Surfactant(s): | | | | | |
| Igepal CO 630 | 0.05 | 0.15 | 0.3 | 0.05 | 0.15 |
| Gafac RE 610 | 0 | 0 | 0 | 0.05 | 0.15 |
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0.05 | 0.15 | 0.3 | 0.1 | 0.3 |
| Stability: | | | | | |
| Time, observation at ambient conditions | | | | | |
| 0 time | cloudy | cloudy | cloudy | cloudy | hazy |
| 1 day | | | | | |
| 2 days | | | | | |
| 4 days | cloudy | cloudy | cloudy | hazy | clear |
| 1 week | cloudy | cloudy | cloudy | hazy | clear |
| 2 weeks | | | | | |
| 4 weeks | | | | | |
| 6 weeks | | | | | |
| 2 months | | | | | |
| 4 months | | | | | |
| 6 months | | | | | |

| Run No. | 21 | 22 | 23 | 24 | 25 |
|---|---|---|---|---|---|
| Active Ingredient(s): | | | | | |
| D-Allethrin | 0.05 | 0.05 | 0.05 | 0.05 | 0.05 |
| Tetramethrin | 0 | 0 | 0 | 0 | 0 |
| Permethrine | 0 | 0 | 0 | 0 | 0 |
| Piperonyl Butoxide | 0 | 0 | 0 | 0 | 0 |
| Lactam(s): | | | | | |
| N-Methylpyrrolidone | 0.45 | 0.45 | 0.45 | 0.45 | 0.45 |
| N-Octylpyrrolidone | 0 | 0.03 | 0.1 | 0.2 | 0.3 |
| Surfactant(s): | | | | | |
| Igepal CO 630 | 0.3 | 0.03 | 0.1 | 0.2 | 0.3 |
| Gafac RE 610 | 0.3 | 0.03 | 0.1 | 0.2 | 0.3 |
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0.6 | 0.06 | 0.2 | 0.4 | 0.6 |
| Stability: | | | | | |
| Time, observation at ambient conditions | | | | | |
| 0 time | clear | cloudy | clear | clear | clear |
| 1 day | | | | | |
| 2 days | | | | | |
| 4 days | clear | cloudy | clear | clear | clear |
| 1 week | clear | cloudy | clear | sl hazy | clear |
| 2 weeks | | | clear | | |
| 4 weeks | | | clear | | |
| 6 weeks | | | clear | | |
| 2 months | | | clear | | |
| 4 months | | | clear | | |
| 6 months | | | clear | | |

| Run No. | 26 | 27 | 28 |
|---|---|---|---|
| Active Ingredient(s): | | | |
| D-Allethrin | 0.05 | 0.05 | 0.05 |
| Tetramethrin | 0 | 0 | 0 |
| Permethrine | 0 | 0 | 0 |
| Piperonyl Butoxide | 0 | 0 | 0 |
| Lactam(s): | | | |
| N-Methylpyrrolidone | 0.45 | 0.45 | 0.45 |
| N-Octylpyrrolidone | 0.06 | 0.13 | 0.16 |
| Surfactant(s): | | | |
| Igepal CO 630 | 0.06 | 0.13 | 0.16 |
| Gafac RE 610 | 0.06 | 0.13 | 0.16 |
| Pegol L 31 | 0 | 0 | 0 |
| Sodium Dodecyl Sulfate | 0 | 0 | 0 |
| *diluted to 100% with | h | h | h |
| Total Surfactants | 0.12 | 0.26 | 0.32 |
| Stability: | | | |
| Time, observation at ambient conditions | | | |
| 0 time | clear | clear | clear |
| 1 day | | | |
| 2 days | | | |
| 4 days | | | |
| 1 week | hazy | clear | clear |
| 2 weeks | | | |
| 4 weeks | | | |
| 6 weeks | | | |
| 2 months | | | |
| 4 months | | | |
| 6 months | | | |

*h, means 342 ppm standard hard water;
d, means deionized water.

TABLE 2

Microemulsion Composition for Permethrin (Percentage by weight) and Stability

| Run No. | 29 | 30 | 31 | 32 | 33 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |

TABLE 2-continued

Microemulsion Composition for Permethrin (Percentage by weight) and Stability

| | | | | | |
|---|---|---|---|---|---|
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 0 | 0 | 1 | 0 | 0 |
| Surfactant(s): | | | | | |
| Igepal CO 630 | 1 | 0 | 0 | 2 | 0 |
| Gafac RE 610 | 0 | 1 | 0 | 0 | 2 |
| Pegol L 31 | 0 | 0 | 0 | 0 | 0 |
| Sodium Dodecyl Sulfate | 0 | 0 | 0 | 0 | 0 |
| *diluted to 100% with | d | d | d | d | d |
| Total Surfactants | 1 | 1 | 0 | 2 | 2 |
| Stability: | | | | | |
| Time, observation at ambient conditions | | | | | |
| 0 time | clear | cloudy | cloudy | clear | clear |
| 1 day | | | | | |
| 2 days | clear | cloudy | cloudy | clear | clear |
| 4 days | clear | cloudy | cloudy | clear | clear |
| 1 week | clear | | clear | clear | |
| 2 weeks | | | clear | | |
| 4 weeks | | | | | |
| 6 weeks | | | | | |
| 2 months | | | | | |
| 4 months | | | | | |
| 6 months | | | | | |

| Run No. | 34 | 35 | 36 | 37 | 38 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 2 | 0 | 0 | 0 | 0 |
| Surfactant(s): | | | | | |
| Igepal CO 630 | 0 | 1 | 2 | 0 | 0.5 |
| Gafac RE 610 | 0 | 0 | 0 | 2 | 0.5 |
| Pegol L 31 | 0 | 0 | 0 | 0 | 0 |
| Sodium Dodecyl Sulfate | 0 | 0 | 0 | 0 | 0 |
| *diluted to 100% with | d | h | h | h | d |
| Total Surfactants | 0 | 1 | 2 | 2 | 1 |
| Stability: | | | | | |
| Time, observation at ambient conditions | | | | | |
| 0 time | cloudy | clear | clear | clear | hazy |
| 1 day | | | | | |
| 2 days | cloudy | | | | |
| 4 days | cloudy | | | | cloudy |
| 1 week | | clear | | | |
| 2 weeks | | | clear | clear | |
| 4 weeks | | | | | |
| 6 weeks | | | | | |
| 2 months | | | | | |
| 4 months | | | | | |
| 6 months | | | | | |

| Run No. | 39 | 40 | 41 | 42 | 43 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 0.5 | 0.5 | 0 | 1 | 1 |
| Surfactant(s): | | | | | |
| Igepal CO 630 | 0.5 | 0 | 1 | 1 | 0 |
| Gafac RE 610 | 0 | 0.5 | 1 | 0 | 1 |
| Pegol L 31 | 0 | 0 | 0 | 0 | 0 |
| Sodium Dodecyl Sulfate | 0 | 0 | 0 | 0 | 0 |
| *diluted to 100% with | d | d | d | d | d |
| Total Surfactants | 0.5 | 0.5 | 2 | 1 | 1 |
| Stability: | | | | | |
| Time, observation at ambient conditions | | | | | |
| 0 time | cloudy | cloudy | clear | cloudy | cloudy |
| 1 day | | | | | |
| 2 days | | | | | |
| 4 days | | | cloudy | cloudy | hazy |
| 1 week | | | clear | | clear |
| 2 weeks | | | clear | | |
| 4 weeks | | | | | |
| 6 weeks | | | | | |
| 2 months | | | | | |
| 4 months | | | | | |
| 6 months | | | | | |

| Run No. | 44 | 45 | 46 | 47 | 48 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 1 | 1 | 0.33 | 0.25 | 0.2 |
| Surfactant(s): | | | | | |
| Igepal CO 630 | 1 | 0 | 0.33 | 0.5 | 0.6 |
| Gafac RE 610 | 0 | 1 | 0.33 | 0.25 | 0.2 |
| Pegol L 31 | 0 | 0 | 0 | 0 | 0 |
| Sodium Dodecyl Sulfate | 0 | 0 | 0 | 0 | 0 |
| *diluted to 100% with | h | h | d | d | d |
| Total Surfactants | 1 | 1 | 0.66 | 0.75 | 0.8 |
| Stability: | | | | | |
| Time, observation at ambient conditions | | | | | |
| 0 time | clear | cloudy | cloudy | clear | cloudy |
| 1 day | clear | | cloudy | clear | clear |
| 2 days | clear | | cloudy | clear | clear |
| 4 days | clear | | hazy | clear | clear |
| 1 week | clear | | clear | clear | clear |
| 2 weeks | clear | | | clear | clear |
| 4 weeks | | | | | |
| 6 weeks | | | | | |
| 2 months | | | | | |
| 4 months | | | | | |
| 6 months | | | | | |

| Run No. | 49 | 50 | 51 | 52 | 53 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 0.16 | 0.66 | 0.5 | 0.4 | 0.3 |
| Surfactant(s): | | | | | |
| Igepal CO 630 | 0.66 | 0.66 | 1 | 1.2 | 1.33 |
| Gafac RE 610 | 0.16 | 0.66 | 0.5 | 0.4 | 0.3 |
| Pegol L 31 | 0 | 0 | 0 | 0 | 0 |
| Sodium Dodecyl Sulfate | 0 | 0 | 0 | 0 | 0 |
| *diluted to 100% with | d | d | d | d | d |
| Total Surfactants | 0.82 | 1.32 | 1.5 | 1.6 | 1.63 |
| Stability: | | | | | |
| Time, observation at ambient conditions | | | | | |
| 0 time | cloudy | cloudy | cloudy | cloudy | cloudy |
| 1 day | | | clear | clear | |
| 2 days | | | clear | clear | |
| 4 days | cloudy | hazy | clear | clear | clear |
| 1 week | | clear | clear | clear | clear |
| 2 weeks | | | | | |
| 4 weeks | | | | | |
| 6 weeks | | | | | |
| 2 months | | | | | |
| 4 months | | | | | |
| 6 months | | | | | |

| Run No. | 54 | 55 | 56 | 57 | 58 |
|---|---|---|---|---|---|
| Active Ingredient(s): | | | | | |

TABLE 2-continued
Microemulsion Composition for Permethrin
(Percentage by weight) and Stability

| | | | | | |
|---|---|---|---|---|---|
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 1.35 | 1.35 | 1.35 |
| N-Octylpyrrolidone | 0.3 | 0.25 | 0.2 | 0.6 | 0.5 |
| Surfactant(s): | | | | | |
| Igepal CO 630 | 0.33 | 0.5 | 0.6 | 0.6 | 1 |
| Gafac RE 610 | 0.3 | 0.25 | 0.2 | 0.6 | 0.5 |
| Pegol L 31 | 0 | 0 | 0 | 0 | 0 |
| Sodium Dodecyl Sulfate | 0 | 0 | 0 | 0 | 0 |
| *diluted to 100% with | h | h | h | h | h |
| Total Surfactants | 0.63 | 0.75 | 0.8 | 1.2 | 1.5 |
| Stability: | | | | | |
| Time, observation at ambient conditions | | | | | |
| 0 time | hazy | hazy | cloudy | cloudy | clear |
| 1 day | clear | clear | cloudy | clear | clear |
| 2 days | clear | clear | cloudy | clear | clear |
| 4 days | | | | | clear |
| 1 week | | | | | clear |
| 2 weeks | | | | | clear |
| 4 weeks | | | | | clear |
| 6 weeks | | | | | clear |
| 2 months | | | | | |
| 4 months | | | | | |
| 6 months | | | | | |

| Run No. | 59 | 60 | 61 | 62 | 63 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrin | 0.15 | 0.15 | 0.15 | 0.15 | 0.15 |
| Piperonyl Butoxide | 0 | 0 | 0 | 0 | 0 |
| Lactam(s): | | | | | |
| N-Methylpyrrolidone | 1.35 | 1.35 | 0 | 0 | 0 |
| N-Octylpyrrolidone | 0.4 | 0.33 | 10 | 0 | 5 |
| Surfactant(s): | | | | | |
| Igepal CO 630 | 1.2 | 1.33 | 0 | 0 | 1 |
| Gafac RE 610 | 0.4 | 0.33 | 0 | 0 | 0 |
| Pegol L 31 | 0 | 0 | 0 | 0 | 0 |
| Sodium Dodecyl Sulfate | 0 | 0 | 1 | 1 | 1 |
| *diluted to 100% with | h | h | d | d | d |
| Total Surfactants | 1.6 | 1.66 | 1 | 1 | 2 |
| Stability: | | | | | |
| Time, observation at ambient conditions | | | | | |
| 0 time | clear | cloudy | gel | ppt | cloudy |
| 1 day | clear | clear | gel | pcpt | hazy |
| 2 days | clear | clear | gel | pcpt | hazy |
| 4 days | clear | | vl | pcpt | tp |
| 1 week | clear | | | | |
| 2 weeks | clear | | | | |
| 4 weeks | clear | | | | |
| 6 weeks | | | | | |
| 2 months | | | | | |
| 4 months | | | | | |
| 6 months | | | | | |

| Run No. | 64 | 65 |
|---|---|---|
| Active Ingredient(s): | | |
| D-Allethrin | 0 | 0 |
| Tetramethrin | 0 | 0 |
| Permethrin | 0.15 | 0.15 |
| Piperonyl Butoxide | 0 | 0 |
| Lactam(s): | | |
| N-Methylpyrrolidone | 0 | 0 |
| N-Octylpyrrolidone | 5 | 0 |
| Surfactant(s): | | |
| Igepal CO 630 | 0 | 0 |
| Gafac RE 610 | 0 | 0 |
| Pegol L 31 | 0 | 0 |
| Sodium Dodecyl Sulfate | 2 | 2 |
| *diluted to 100% with | d | d |
| Total Surfactants | 2 | 2 |
| Stability: | | |
| Time, observation at ambient conditions | | |
| 0 time | clear | insoluble |
| 1 day | clear | insoluble |
| 2 days | clear | insoluble |
| 4 days | clear | |
| 1 week | clear | |
| 2 weeks | clear | |
| 4 weeks | | |
| 6 weeks | | |
| 2 months | | |
| 4 months | | |
| 6 months | | |

*vl means viscous liquid;
tp means two phases
*h, means 342 ppm standard hard water;
d, means deionized water

TABLE 3
Microemulsion Composition for Piperonyl Butoxide
(Percent by weight) and Stability

| Run No. | 66 | 67 | 68 | 69 | 70 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrine | 0 | 0 | 0 | 0 | 0 |
| Piperonyl Butoxide | 1 | 1 | 1 | 1 | 1 |
| Lactam(s): | | | | | |
| N-Methylpyrrolidone | 10 | 10 | 10 | 10 | 0 |
| N-Octylpyrrolidone | 0 | 1.25 | 1.66 | 0.625 | 0 |
| Surfactant(s): | | | | | |
| Igepal CO 630 | 5 | 2.5 | 1.66 | 3.75 | 5 |
| Gafac RE 610 | 0 | 1.25 | 1.66 | 0 | 0 |
| Pegol L 31 | 0 | 0 | 0 | 0.625 | 0 |
| Sodium Dodecyl Sulfate | 0 | 0 | 0 | 0 | 0 |
| *diluted to 100% with | d | d | d | d | d |
| Total Surfactants | 5 | 3.75 | 3.32 | 4.375 | 5 |
| Stability: | | | | | |
| Time, observation at ambient conditions | | | | | |
| 0 time | clear | clear | clear | clear | clear |
| 1 day | clear | clear | clear | clear | hazy |
| 5 days | clear | clear | clear | clear | |
| 1 week | clear | clear | clear | clear | |
| 2 weeks | clear | clear | clear | clear | |
| 4 weeks | | | | | |
| 6 weeks | clear | clear | clear | clear | |
| 2 months | | | | | |
| 4 months | | | | | |
| 6 months | | | | | |

| Run No. | 71 | 72 | 73 | 74 | 75 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrine | 0 | 0 | 0 | 0 | 0 |
| Piperonyl Butoxide | 1 | 1 | 1 | 1 | 1 |
| Lactam(s): | | | | | |
| N-Methylpyrrolidone | 0 | 0 | 0 | 2 | 2 |
| N-Octylpyrrolidone | 1.25 | 1.6 | 0.625 | 0 | 1.25 |
| Surfactant(s): | | | | | |
| Igepal CO 630 | 2.5 | 1.6 | 3.75 | 5 | 2.5 |
| Gafac RE 610 | 1.25 | 1.6 | 0.625 | 0 | 1.25 |
| Pegol L 31 | 0 | 0 | 0 | 0 | 0 |
| Sodium Dodecyl Sulfate | 0 | 0 | 0 | 0 | 0 |
| *diluted to 100% with | d | d | d | d | d |
| Total Surfactants | 3.75 | 3.2 | 4.375 | 5 | 3.75 |
| Stability: | | | | | |
| Time, observation at ambient conditions | | | | | |
| 0 time | cloudy | cloudy | cloudy | clear | cloudy |
| 1 day | cloudy | cloudy | cloudy | clear | cloudy |
| 5 days | cloudy | cloudy | cloudy | clear | cloudy |
| 1 week | cloudy | cloudy | cloudy | clear | cloudy |
| 2 weeks | cloudy | cloudy | cloudy | clear | cloudy |

TABLE 3-continued
Microemulsion Composition for Piperonyl Butoxide (Percent by weight) and Stability

| | | | | | |
|---|---|---|---|---|---|
| 4 weeks | | | | | |
| 6 weeks | cloudy | cloudy | cloudy | clear | cloudy |
| 2 months | | | | | |
| 4 months | | | | | |
| 6 months | | | | | |

| Run No. | 76 | 77 | 78 | 79 | 80 |
|---|---|---|---|---|---|
| Active Ingredient(s): | | | | | |
| D-Allethrin | 0 | 0 | 0 | 0 | 0 |
| Tetramethrin | 0 | 0 | 0 | 0 | 0 |
| Permethrine | 0 | 0 | 0 | 0 | 0 |
| Piperonyl Butoxide | 1 | 1 | 1 | 1 | 1 |
| Lactam(s): | | | | | |
| N-Methylpyrrolidone | 2 | 2 | 5 | 5 | 5 |
| N-Octylpyrrolidone | 1.66 | 0.625 | 0 | 1.25 | 1.66 |
| Surfactant(s): | | | | | |
| Igepal CO 630 | 1.66 | 3.75 | 5 | 2.5 | 1.66 |
| Gafac RE 610 | 1.66 | 0 | 0 | 1.25 | 1.66 |
| Pegol L 31 | 0 | 0.625 | 0 | 0 | 0 |
| Sodium Dodecyl Sulfate | 0 | 0 | 0 | 0 | 0 |
| *diluted to 100% with | d | d | d | d | d |
| Total Surfactants | 3.32 | 4.375 | 5 | 3.75 | 3.32 |
| Stability: | | | | | |
| Time, observation at ambient conditions | | | | | |
| 0 time | clear | clear | clear | clear | clear |
| 1 day | clear | clear | clear | clear | clear |
| 5 days | clear | clear | clear | clear | clear |
| 1 week | clear | clear | clear | clear | clear |
| 2 weeks | clear | clear | clear | clear | clear |
| 4 weeks | | | | | |
| 6 weeks | clear | clear | clear | clear | clear |
| 2 months | | | | | |
| 4 months | | | | | |
| 6 months | | | | | |

| Run No. | 81 |
|---|---|
| Active Ingredient(s): | |
| D-Allethrin | 0 |
| Tetramethrin | 0 |
| Permethrine | 0 |
| Piperonyl Butoxide | 1 |
| Lactam(s): | |
| N-Methylpyrrolidone | 5 |
| N-Octylpyrrolidone | 0.625 |
| Surfactant(s): | |
| Igepal CO 630 | 3.75 |
| Gafac RE 610 | 0 |
| Pegol L 31 | 0.625 |
| Sodium Dodecyl Sulfate | 0 |
| *diluted to 100 % with | d |
| Total Surfactants | 4.375 |
| Stability: | |
| Time, observation at ambient conditions | |
| 0 time | clear |
| 1 day | |
| 5 days | |
| 1 week | |
| 2 weeks | |
| 4 weeks | |
| 6 weeks | clear |
| 2 months | |
| 4 months | |
| 6 months | |

*h, means 342 ppm standard hard water; d, means deionized water

TABLE 4
Microemulsion Composition for Tetramethrin (Percent by weight) and Stability

| Run No. | 82 | 83 | 84 | 85 | 86 | 87 | 88 | 89 | 90 | 91 | 92 | 93 | 94 |
|---|---|---|---|---|---|---|---|---|---|---|---|---|---|
| Active Ingredient(s): | | | | | | | | | | | | | |
| D-Allethrin | 0 | 0 | 0 | 0 | 0 | 0 | 0 | 0 | 0 | 0 | 0 | 0 | 0 |
| Tetramethrin | 0.2 | 0.2 | 0.2 | 0.2 | 0.2 | 0.2 | 0.2 | 0.2 | 0.2 | 0.2 | 0.2 | 0.2 | 0.2 |
| Permethrine | 0 | 0 | 0 | 0 | 0 | 0 | 0 | 0 | 0 | 0 | 0 | 0 | 0 |
| Piperonyl Butoxide | 0 | 0 | 0 | 0 | 0 | 0 | 0 | 0 | 0 | 0 | 0 | 0 | 0 |
| Lactam(s): | | | | | | | | | | | | | |
| N-Methylpyrrolidone | 1.8 | 1.8 | 1.8 | 1.8 | 1.8 | 1.8 | 1.8 | 1.8 | 1.8 | 1.8 | 1.8 | 1.8 | 1.8 |
| N-Octylpyrrolidone | 0 | 0 | 1 | 0 | 0 | 0 | 0 | 0 | 0 | 0 | 0 | 0.5 | 0.5 |
| Surfactant(s): | | | | | | | | | | | | | |
| Igepal CO 630 | 1 | 0 | 0 | 0 | 0 | 2 | 5 | 5 | 2 | 5 | 0.5 | 0.5 | 0 |
| Gafac RE 610 | 0 | 1 | 0 | 0 | 0 | 0 | 0 | 0 | 0 | 0.5 | 0.5 | 0 | 0.5 |
| Pegol L 31 | 0 | 0 | 0 | 1 | 0 | 0 | 0 | 0 | 0 | 0 | 0 | 0 | 0 |
| Aerosol OTB | 0 | 0 | 0 | 0 | 1 | 0 | 0 | 0 | 0 | 0 | 0 | 0 | 0 |
| *diluted to 100% with | h | h | h | d | d | d | d | d | d | h | h | h | h |
| Total Surfactants | 1 | 1 | 0 | 1 | 1 | 2 | 5 | 5 | 2 | 5.5 | 1 | 0.5 | 0.5 |
| Stability: | | | | | | | | | | | | | |
| Time, observation at ambient conditions | | | | | | | | | | | | | |
| 0 time | clear | cloudy | cloudy | cloudy | cloudy | clear | clear | clear | clear | clear | cloudy | cloudy | cloudy |
| 1 day | cloudy | cloudy | cloudy | cloudy | cloudy | | | | | clear | crystals | cloudy | cloudy |
| 2 days | | | | | | | | clear | crystals | clear | | | |
| 6 days | | | | pcpt | pcpt | clear | clear | crystals | crystals | pcpt | | | |
| 2 weeks | | | | | | | | | | | | | |
| 3 weeks | | | | | | | | | | | | | |
| 6 weeks | | | | | | | | | | | | | |
| 2 months | | | | | | | | | | | | | |
| 4 months | | | | | | | | | | | | | |
| 6 months | | | | | | | | | | | | | |

| Run No. | 95 | 96 | 97 | 98 | 99 | 100 | 101 | 102 | 103 | 104 | 105 | 106 |
|---|---|---|---|---|---|---|---|---|---|---|---|---|
| Active Ingredient(s): | | | | | | | | | | | | |
| D-Allethrin | 0 | 0 | 0 | 0 | 0 | 0 | 0 | 0 | 0 | 0 | 0 | 0 |
| Tetramethrin | 0.2 | 0.2 | 0.2 | 0.2 | 0.2 | 0.2 | 0.2 | 0.2 | 0.2 | 0.2 | 0.2 | 0.2 |
| Permethrine | 0 | 0 | 0 | 0 | 0 | 0 | 0 | 0 | 0 | 0 | 0 | 0 |
| Piperonyl Butoxide | 0 | 0 | 0 | 0 | 0 | 0 | 0 | 0 | 0 | 0 | 0 | 0 |
| Lactam(s): | | | | | | | | | | | | |
| N-Methylpyrrolidone | 1.8 | 1.8 | 1.8 | 1.8 | 1.8 | 1.8 | 1.8 | 1.8 | 1.8 | 1.8 | 1.8 | 1.8 |
| N-Octylpyrrolidone | 0 | 0.5 | 0.5 | 0 | 0 | 0.066 | 0.13 | 0.2 | 0.266 | 0.33 | 0.33 | 0.4 |

TABLE 4-continued

Microemulsion Composition for Tetramethrin (Percent by weight) and Stability

| Surfactant(s): | | | | | | | | | | | | |
|---|---|---|---|---|---|---|---|---|---|---|---|---|
| Igepal CO 630 | 0.5 | 0 | 0 | 0.5 | 0 | 0.066 | 0.133 | 0.2 | 0.266 | 0.33 | 0.33 | 0.4 |
| Gafac RE 610 | 0 | 0 | 0 | 0 | 0 | 0.066 | 0.133 | 0.2 | 0.266 | 0.33 | 0.33 | 0.4 |
| Pegol L 31 | 0.5 | 0.5 | 0 | 0 | 0 | 0 | 0 | 0 | 0 | 0 | 0 | 0 |
| Aerosol OTB | 0 | 0 | 0.5 | 0.5 | 0 | 0 | 0 | 0 | 0 | 0 | 0 | 0 |
| *diluted to 100% with | d | d | d | d | h | h | h | h | h | h | d | h |
| Total Surfactants | 1 | 0.5 | 0.5 | 1 | 0 | 0.132 | 0.266 | 0.4 | 0.532 | 0.66 | 0.66 | 0.8 |
| Stability: | | | | | | | | | | | | |
| Time, observation at ambient conditions | | | | | | | | | | | | |
| 0 time | cloudy | cloudy | cloudy | cloudy | sediment | sediment | sediment | clear | hazy | hazy | hazy | hazy |
| 1 day | cloudy | cloudy | cloudy | cloudy | sediment | sediment | sediment | crystals | pcpt | cloudy | | pcpt |
| 2 days | | | | | | | | | | | cloudy | |
| 6 days | | | | | | | | | | | | |
| 2 weeks | | | | | | | | | | | | |
| 3 weeks | | | | | | | | | | | | |
| 6 weeks | | | | | | | | | | | | |
| 2 months | | | | | | | | | | | | |
| 4 months | | | | | | | | | | | | |
| 6 months | | | | | | | | | | | | |

| Run No. | 107 | 108 | 109 | 110 | 111 | 112 | 113 | 114 | 115 | 116 | 117 | 118 | 119 |
|---|---|---|---|---|---|---|---|---|---|---|---|---|---|
| Active Ingredient(s): | | | | | | | | | | | | | |
| D-Allethrin | 0 | 0 | 0 | 0 | 0 | 0 | 0 | 0 | 0 | 0 | 0 | 0 | 0 |
| Tetramethrin | 0.2 | 0.2 | 0.2 | 0.2 | 0.2 | 0.2 | 0.2 | 0.2 | 0.2 | 0.2 | 0.2 | 0.2 | 0.2 |
| Permethrine | 0 | 0 | 0 | 0 | 0 | 0 | 0 | 0 | 0 | 0 | 0 | 0 | 0 |
| Piperonyl Butoxide | 0 | 0 | 0 | 0 | 0 | 0 | 0 | 0 | 0 | 0 | 0 | 0 | 0 |
| Lactam(s): | | | | | | | | | | | | | |
| N-Methylpyrrolidone | 1.8 | 1.8 | 1.8 | 1.8 | 1.8 | 1.8 | 1.8 | 1.8 | 1.8 | 1.8 | 1.8 | 1.8 | 1.8 |
| N-Octylpyrrolidone | 0.33 | 0.33 | 0.25 | 0.2 | 0.166 | 0.33 | 0.25 | 0.2 | 0.166 | 0.66 | 0.5 | 0.4 | 0.25 |
| Surfactant(s): | | | | | | | | | | | | | |
| Igepal CO 630 | 0.33 | 0.33 | 0.5 | 0.6 | 0.66 | 0.33 | 0.5 | 0.6 | 0.66 | 0.66 | 1 | 1.2 | 1.5 |
| Gafac RE 610 | 0.33 | 0 | 0 | 0 | 0 | 0 | 0 | 0 | 0 | 0 | 0 | 0 | 0 |
| Pegol L 31 | 0 | 0 | 0 | 0 | 0 | 0.33 | 0.25 | 0.2 | 0.166 | 0.66 | 0.5 | 0.4 | 0.25 |
| Aerosol OTB | 0 | 0.33 | 0.25 | 0.2 | 0.166 | 0 | 0 | 0 | 0 | 0 | 0 | 0 | 0 |
| *diluted to 100% with | h | d | d | d | d | d | d | d | d | d | d | d | d |
| Total Surfactants | 0.66 | 0.66 | 0.75 | 0.8 | 0.826 | 0.66 | 0.75 | 0.8 | 0.826 | 1.32 | 1.5 | 1.6 | 1.75 |
| Stability: | | | | | | | | | | | | | |
| Time, observation at ambient conditions | | | | | | | | | | | | | |
| 0 time | clear | cloudy | cloudy | cloudy | cloudy | cloudy | clear | cloudy | cloudy | hazy | cloudy | cloudy | clear |
| 1 day | pcpt | cloudy | cloudy | cloudy | cloudy | cloudy | cloudy | cloudy | cloudy | | | | |
| 2 days | | | | | | | | | | cloudy | cloudy | cloudy | crystals |
| 6 days | | | | | | | | | | cloudy | cloudy | cloudy | crystals |
| 2 weeks | | | | | | | | | | | | | |
| 3 weeks | | | | | | | | | | | | | |
| 6 weeks | | | | | | | | | | | | | |
| 2 months | | | | | | | | | | | | | |
| 4 months | | | | | | | | | | | | | |
| 6 months | | | | | | | | | | | | | |

| Run No. | 120 | 121 | 122 | 123 | 124 | 125 | 126 | 127 | 128 |
|---|---|---|---|---|---|---|---|---|---|
| Active Ingredient(s): | | | | | | | | | |
| D-Allethrin | 0 | 0 | 0 | 0 | 0 | 0 | 0 | 0 | 0 |
| Tetramethrin | 0.2 | 0.2 | 0.2 | 0.2 | 0.2 | 0.2 | 0.2 | 0.2 | 0.2 |
| Permethrine | 0 | 0 | 0 | 0 | 0 | 0 | 0 | 0 | 0 |
| Piperonyl Butoxide | 0 | 0 | 0 | 0 | 0 | 0 | 0 | 0 | 0 |
| Lactam(s): | | | | | | | | | |
| N-Methylpyrrolidone | 1.8 | 1.8 | 1.8 | 1.8 | 1.8 | 1.8 | 1.8 | 1.8 | 1.8 |
| N-Octylpyrrolidone | 1 | 0.75 | 0.5 | 0.375 | 1.6 | 1.25 | 0.833 | 0.625 | 0.625 |
| Surfactant(s): | | | | | | | | | |
| Igepal CO 630 | 1 | 1.5 | 2 | 2.25 | 1.6 | 2.5 | 3.33 | 3.75 | 3.75 |
| Gafac RE 610 | 0 | 0 | 0 | 0 | 0 | 0 | 0 | 0 | 0 |
| Pegol L 31 | 1 | 0.75 | 0.5 | 0.375 | 1.6 | 1.25 | 0.833 | 0.625 | 0.625 |
| Aerosol OTB | 0 | 0 | 0 | 0 | 0 | 0 | 0 | 0 | 0 |
| *diluted to 100% with | d | d | d | d | d | d | d | d | h |
| Total Surfactants | 2 | 2.25 | 2.5 | 2.625 | 3.2 | 3.75 | 4.163 | 4.375 | 4.375 |
| Stability: | | | | | | | | | |
| Time, observation at ambient conditions | | | | | | | | | |
| 0 time | cloudy | clear | hazy | clear | cloudy | cloudy | sl hazy | clear | clear |
| 1 day | | | | | | | | | clear |
| 2 days | cloudy | crystals | hazy | clear | two phase | two phase | sl hazy | clear | clear |
| 6 days | cloudy | crystals | hazy | crystals | two phase | two phase | sl hazy | clear | clear |
| 2 weeks | | | | | | | | clear | clear |
| 3 weeks | | | | | | | | clear | clear |
| 6 weeks | | | | | | | | clear | clear |
| 2 months | | | | | | | | clear | |

TABLE 4-continued

| Microemulsion Composition for Tetramethrin (Percent by weight) and Stability | |
|---|---|
| 4 months | clear |
| 6 months | |

* h, means 342 ppm standard hard water; d, means deionized water.

TABLE 5

Microemulsion Composition Contrary Four Active Ingredients (Percent by weight) and Stability

| Run No. | 129 | 130 | 131 | 132 | 133 | 134 | 135 | 136 | 137** | 138 | 139 | 140 | 141 | 142 | 143 | 144 |
|---|---|---|---|---|---|---|---|---|---|---|---|---|---|---|---|---|
| Active Ingredient(s): | | | | | | | | | | | | | | | | |
| D-Allethrin | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Tetramethrin | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Permethrine | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |
| Piperonyl Butoxide | 1 | 1 | 1 | 1 | 1 | 1 | 1 | 1 | 1 | 1 | 1 | 1 | 1 | 1 | 1 | 1 |
| Lactam(s): | | | | | | | | | | | | | | | | |
| N-Methylpyrrolidone | 10 | 10 | 10 | 10 | 0 | 0 | 2 | 5 | 5 | 10 | 2 | 5 | 5 | 5 | 5 | 5 |
| N-Octylpyrrolidone | 0 | 1.25 | 1.66 | 0.625 | 0.625 | 0 | 0 | 0 | 0.625 | 0.625 | 0 | 0 | 0.625 | 0.625 | 0.625 | 0.625 |
| Polymer(s): | | | | | | | | | | | | | | | | |
| PVP | 0 | 0 | 0 | 0 | 0 | 0 | 0 | 0 | 0 | 0 | 0 | 0 | 0 | 0.5 | 0.5 | 0 |
| PVP/VA S 630 | 0 | 0 | 0 | 0 | 0 | 0 | 0 | 0 | 0 | 0 | 0 | 0 | 0 | 0 | 0 | 0.5 |
| Surfactant(s): | | | | | | | | | | | | | | | | |
| Igepal CO 630 | 5 | 2.5 | 1.66 | 3.75 | 3.75 | 5 | 5 | 5 | 3.75 | 3.75 | 5 | 5 | 3.75 | 3.75 | 3.75 | 3.75 |
| Gafac RE 610 | 0 | 1.25 | 1.66 | 0 | 0 | 0 | 0 | 0 | 0 | 0 | 0 | 0 | 0 | 0 | 0 | 0 |
| Pegol L 31 | 0 | 0 | 0 | 0.625 | 0.625 | 0 | 0 | 0 | 0.625 | 0.625 | 0 | 0 | 0.625 | 0.625 | 0.625 | 0.625 |
| Sodium Dodecyl Sulfate | 0 | 0 | 0 | 0 | 0 | 0 | 0 | 0 | 0 | 0 | 0 | 0 | 0 | 0 | 0 | 0 |
| *diluted to 100% with | d | d | d | d | d | d | d | d | d | h | h | h | h | d | h | d |
| Made from concentrate? | no | no | no | no | no | no | no | no | no | no | no | no | no | yes | yes | yes |
| Total Surfactants | 5 | 3.75 | 3.32 | 4.375 | 4.375 | 5 | 5 | 5 | 4.375 | 4.375 | 5 | 5 | 4.375 | 4.375 | 4.375 | 4.375 |
| Stability: Time, observation at ambient conditions | | | | | | | | | | | | | | | | |
| 0 time | clear | clear | clear | clear | pcpt | pcpt | clear | clear | clear | clear | clear | clear | clear | clear | clear | clear |
| 1 day | | | | | cloudy pcpt | | | | | | | | | | clear | clear |
| 2 days | | | | | cloudy pcpt | | | | | | | | | | | |
| 4 days | clear | clear | clear | clear | cloudy pcpt | pcpt | clear | clear | clear | clear | clear | clear | clear | clear | clear | clear |
| 6 days | clear | clear | clear | clear | cloudy pcpt | pcpt | clear | clear | clear | clear | clear | clear | clear | clear | | |
| 2 weeks | | | | | | | | | | | | | | | clear | clear |
| 4 weeks | clear | clear | clear | clear | | | clear | clear | clear | clear | clear | clear | clear | clear | | |
| 5 weeks | clear | clear | clear | clear | | | clear | clear | clear | clear | clear | clear | clear | clear | clear | clear |
| 2 months | | | | | | | | | | | | clear | | clear | | |
| 4 months | | | | | | | | | clear | | | clear | | | | |
| 6 months | | | | | | | | | clear | | | clear | | | | |

| Run No. | 145 | 146 | 147 | 148 | 149 | 150 | 151 | 152 | 153*** | 154*** | 155*** | 156 | 157 | 158 | 159*** |
|---|---|---|---|---|---|---|---|---|---|---|---|---|---|---|---|
| Active Ingredient(s): | | | | | | | | | | | | | | | |
| D-Allethrin | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Tetramethrin | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Permethrine | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |
| Piperonyl Butoxide | 1 | 1 | 1 | 1 | 1 | 1 | 1 | 1 | 1 | 1 | 1 | 1 | 1 | 1 | 1 |
| Lactam(s): | | | | | | | | | | | | | | | |
| N-Methylpyrrolidone | 5 | 5 | 5 | 10 | 2 | 5 | 5 | 10 | 2 | 5 | 5 | 10 | 10 | 5 | 5 |
| N-Octylpyrrolidone | 0.625 | 0.625 | 0.625 | 0.625 | 0 | 0 | 0.625 | 0.625 | 0 | 0 | 0.625 | 0.625 | 0.625 | 0.625 | 0.625 |
| Polymer(s): | | | | | | | | | | | | | | | |
| PVP | 0 | 0 | 0 | 0.5 | 0.5 | 0.5 | 0.5 | 0.5 | 0.5 | 0.5 | 0.5 | 0 | 0 | 0 | 0 |
| PVP/VA S 630 | 0.5 | 0 | 0 | 0 | 0 | 0 | 0 | 0 | 0 | 0 | 0 | 0.5 | 0.5 | 0.5 | 0.5 |
| Surfactant(s): | | | | | | | | | | | | | | | |
| Igepal CO 630 | 3.75 | 3.75 | 3.75 | 3.75 | 5 | 5 | 3.75 | 3.75 | 5 | 5 | 3.75 | 3.75 | 3.75 | 3.75 | 3.75 |
| Gafac RE 610 | 0 | 0 | 0 | 0 | 0 | 0 | 0 | 0 | 0 | 0 | 0 | 0 | 0 | 0 | 0 |
| Pegol L 31 | 0.625 | 0.625 | 0.625 | 0.625 | 0 | 0 | 0.625 | 0.625 | 0 | 0 | 0.625 | 0.625 | 0.625 | 0.625 | 0.625 |
| Sodium Dodecyl Sulfate | 0 | 0 | 0 | 0 | 0 | 0 | 0 | 0 | 0 | 0 | 0 | 0 | 0 | 0 | 0 |
| *diluted to 100% with | h | d | h | h | h | h | h | d | d | d | d | h | d | h | d |
| Made from concentrate? | yes | yes | yes | no | no | no | no | no | no | no | no | no | no | no | no |
| Total Surfactants | 4.375 | 4.375 | 4.375 | 4.375 | 5 | 5 | 4.375 | 4.375 | 5 | 5 | 4.375 | 4.375 | ·4.375 | 4.375 | 4.375 |
| Stability: Time, observation at ambient conditions | | | | | | | | | | | | | | | |
| 0 time | clear | clear | clear | clear | clear | clear | clear | clear | clear | cloudy | clear | clear | clear | clear | clear |
| 1 day | clear | clear | clear | clear | | | | | | | | | | | |
| 2 days | | | | | | | | | | | | | | | |
| 4 days | clear | clear | clear | clear | clear | clear | clear | clear | clear | clear | clear | clear | clear | clear | clear |
| 6 days | | | | | clear | clear | clear | clear | clear | clear | clear | clear | clear | clear | clear |
| 2 weeks | clear | clear | clear | clear | | | | | | | | | | | |
| 4 weeks | | | | | | | | | | | | | | | |

TABLE 5-continued

Microemulsion Composition Contrary Four Active Ingredients (Percent by weight) and Stability

| | | | | | | | | | | | | | | |
|---|---|---|---|---|---|---|---|---|---|---|---|---|---|---|
| 5 weeks | clear | clear | clear | clear | clear | clear | clear | clear | clear | clear | clear | clear | clear | clear | clear |
| 2 months | | | | | | | | | | | | | | | |
| 4 months | | | | | | | | | | | | clear | | | |
| 6 months | | | | | | | | | | | | | | | clear |

**h, means 342 ppm standard hard water; d, menas deionized water.
**pH was monitered for 1 week, no appreciable change pH @ 4.6
***pH was monitered for 1 week, no appreciable change pH @ 4.4

| Run No. | | 137 | 155 | 159 |
|---|---|---|---|---|
| Stability at Increased Temp. Observations: | | | | |
| Time | Temp. (degrees C.) | | | |
| 0 | 40 | clear | clear | clear |
| 1 day | 40 | cloudy* | cloudy* | cloudy* |
| | 23 | clear | clear | clear |
| | 40 | cloudy* | cloudy* | cloudy* |
| 2 day | 40 | cloudy* | cloudy* | cloudy* |
| | 23 | clear | clear | clear |
| | 40 | cloudy* | cloudy* | cloudy* |
| 3 day | 40 | cloudy* | cloudy* | cloudy* |
| | 23 | clear | clear | clear |
| | 40 | cloudy* | cloudy* | cloudy* |
| 1 week | 40 | cloudy* | cloudy* | cloudy* |
| | 23 | clear | clear | clear |
| | 40 | cloudy* | cloudy* | cloudy* |
| 2 mo. | 40 | cloudy* | cloudy* | cloudy* |
| | 23 | clear | clear | clear |
| | 40 | cloudy* | cloudy* | cloudy* |
| 3 mo. | 40 | cloudy* | cloudy* | cloudy* |
| | 23 | clear | clear | clear |
| | 40 | cloudy* | cloudy* | cloudy* |
| 4 mo. | 40 | cloudy* | cloudy* | cloudy* |
| | 23 | clear | clear | clear |
| | 40 | cloudy* | cloudy* | cloudy* |
| Stability at Reduced Temp Observations: | | | | |
| Time | Temp. (degrees C.) | | | |
| 0 | 7 | clear | clear | clear |
| 1 day | 8 | clear | clear | clear |
| 2 weeks | 8 | clear | clear | clear |
| 4 weeks | 7 | clear | clear | clear |
| 8 weeks | 7 | clear | clear | clear |
| 17 weeks | 1 | pcpt* | clear | pcpt* |
| 17 weeks | 24 | clear | clear | clear |

*Became revisibly clear when brought to 20 to 25 degrees C.

TABLE 6

Microemulsion Composition for Permethrin with Mixed Alkyl Pyrrolidones (Percent by weight) and Stability

| Run No. | 160 | 161 | 162 | 163 | 164 | 165 | 166 | 167 | 168 | 169 | 170 |
|---|---|---|---|---|---|---|---|---|---|---|---|
| Active Ingredient(s): | | | | | | | | | | | |
| D-Allethrin | 0 | 0 | 0 | 0 | 0 | 0 | 0 | 0 | 0 | 0 | 0 |
| Tetramethrin | 0 | 0 | 0 | 0 | 0 | 0 | 0 | 0 | 0 | 0 | 0 |
| Permethrin | 0.15 | 0.15 | 0.15 | 0.15 | 0.15 | 0.15 | 0.15 | 0.15 | 0.15 | 0.15 | 0.15 |
| Piperonyl Butoxide | 0 | 0 | 0 | 0 | 0 | 0 | 0 | 0 | 0 | 0 | 0 |
| Lactam(s): | | | | | | | | | | | |
| N-Methylpyrrolidone | 0 | 0 | 0 | 0 | 0 | 0 | 0 | 0 | 0 | 0 | 0 |
| N-Ethylpyrrolidone | 1.35 | 1.35 | 1.35 | 1.35 | 1.35 | 1.35 | 1.35 | 1.35 | 1.35 | 1.35 | 1.35 |
| N-Butylpyrrolidone | 0 | 0 | 0 | 0 | 0 | 0 | 0 | 0 | 0 | 0 | 0 |
| N-Dodecylpyrrolidone | 0 | 0.4 | 0 | 0 | 0 | 0.4 | 0 | 0 | 0 | 0.6 | 0 |
| N-Octylpyrrolidone | 0.4 | 0 | 0 | 0 | 0.4 | 0 | 0 | 0 | 0.6 | 0 | 0 |
| Isooctylpyrrolidone | 0 | 0 | 0.4 | 0 | 0 | 0 | 0.4 | 0 | 0 | 0 | 0.6 |
| Tallowpyrrolidone | 0 | 0 | 0 | 0.4 | 0 | 0 | 0 | 0.4 | 0 | 0 | 0 |
| Surfactant(s): | | | | | | | | | | | |
| Igepal CO 630 | 1.2 | 1.2 | 1.2 | 1.2 | 1.2 | 1.2 | 1.2 | 1.2 | 1.8 | 1.8 | 1.8 |
| Gafac RE 610 | 0.4 | 0.4 | 0.4 | 0.4 | 0.4 | 0.4 | 0.4 | 0.4 | 0.6 | 0.6 | 0.6 |
| *diluted to 100% with | d | d | d | d | h | h | h | h | d | d | d |
| Total Surfactants | 1.6 | 1.6 | 1.6 | 1.6 | 1.6 | 1.6 | 1.6 | 1.6 | 2.4 | 2.4 | 2.4 |
| Stability: Time, observation at ambient conditions | | | | | | | | | | | |
| 0 time | clear | cloudy | cloudy | cloudy | clear | cloudy | cloudy | cloudy | clear | cloudy | cloudy |
| 1 day | clear | cloudy | clear | cloudy pcpt | clear | cloudy | clear | cloudy | clear | cloudy | clear |
| 2 days | | | | | | | | | | | |
| 4 days | | | | | | | | | cloudy | | |
| 6 days | clear | cloudy | clear | cloudy pcpt | clear | cloudy | clear | pcpt | clear | cloudy | clear |

TABLE 6-continued

Microemulsion Composition for Permethrin with Mixed Alkyl Pyrrolidones (Percent by weight) and Stability

| | | | | | | | | | | | |
|---|---|---|---|---|---|---|---|---|---|---|---|
| 2 weeks | | | | | | | | | | | |
| 4 weeks | | | | | | | | | | | |
| 6 weeks | | | | | | | | | | | |
| 2 months | | | | | | | | cloudy | | | |
| 3 months | clear | cloudy | clear | cloudy | pcpt | clear | cloudy | clear | pcpt | clear | cloudy | clear |
| 6 months | | | | | | | | | | | | |

| Run No. | 171 | 172 | 173 | 174 | 175 | 176 | 177 | 178 | 179 | 180 | 181 |
|---|---|---|---|---|---|---|---|---|---|---|---|
| Active Ingredient(s): | | | | | | | | | | | |
| D-Allethrin | 0 | 0 | 0 | 0 | 0 | 0 | 0 | 0 | 0 | 0 | 0 |
| Tetramethrin | 0 | 0 | 0 | 0 | 0 | 0 | 0 | 0 | 0 | 0 | 0 |
| Permethrin | 0.15 | 0.15 | 0.15 | 0.15 | 0.15 | 0.15 | 0.15 | 0.15 | 0.15 | 0.15 | 0.15 |
| Piperonyl Butoxide | 0 | 0 | 0 | 0 | 0 | 0 | 0 | 0 | 0 | 0 | 0 |
| Lactam(s): | | | | | | | | | | | |
| N-Methylpyrrolidone | 0 | 0 | 0 | 0 | 0 | 0 | 0 | 0 | 0 | 0 | 0 |
| N-Ethylpyrrolidone | 1.35 | 1.35 | 1.35 | 1.35 | 1.35 | 0 | 0 | 0 | 0 | 0 | 0 |
| N-Butylpyrrolidone | 0 | 0 | 0 | 0 | 0 | 1.35 | 1.35 | 1.35 | 1.35 | 1.35 | 1.35 |
| N-Dodecylpyrrolidone | 0 | 0 | 0.6 | 0 | 0 | 0 | 0.4 | 0 | 0 | 0 | 0.4 |
| N-Octylpyrrolidone | 0 | 0.6 | 0 | 0 | 0 | 0.4 | 0 | 0 | 0 | 0.4 | 0 |
| Isooctylpyrrolidone | 0 | 0 | 0 | 0.6 | 0 | 0 | 0 | 0.4 | 0 | 0 | 0 |
| Tallowpyrrolidone | 0.6 | 0 | 0 | 0 | 0.6 | 0 | 0 | 0 | 0.4 | 0 | 0 |
| Surfactant(s): | | | | | | | | | | | |
| Igepal CO 630 | 1.8 | 1.8 | 1.8 | 1.8 | 1.8 | 1.2 | 1.2 | 1.2 | 1.2 | 1.2 | 1.2 |
| Gafac RE 610 | 0.6 | 0.6 | 0.6 | 0.6 | 0.6 | 0.4 | 0.4 | 0.4 | 0.4 | 0.4 | 0.4 |
| *diluted to 100% with | d | h | h | h | h | d | d | d | d | h | h |
| Total Surfactants | 2.4 | 2.4 | 2.4 | 2.4 | 2.4 | 1.6 | 1.6 | 1.6 | 1.6 | 1.6 | 1.6 |
| Stability: | | | | | | | | | | | |
| Time, observation at ambient conditions | | | | | | | | | | | |
| 0 time | cloudy | clear | cloudy | cloudy | cloudy | clear | cloudy | clear | cloudy | clear | cloudy |
| 1 day | cloudy | clear | cloudy | clear | cloudy | clear | cloudy | clear | pcpt | clear | cloudy |
| 2 days | | | | | | | | | | | |
| 4 days | | | | | | clear | cloudy | clear | pcpt | clear | cloudy |
| 6 days | cloudy | clear | cloudy | clear | cloudy | | | | | | |
| 2 weeks | | | | | | | | | | | |
| 4 weeks | | | | | | | | | | | |
| 6 weeks | | | | | | | | | | | |
| 2 months | | | | | | | | | | | |
| 3 months | cloudy | clear | cloudy | clear | cloudy | clear | cloudy | clear | pcpt | clear | cloudy |
| 6 months | | | | | | | | | | | |

| Run No. | 182 | 183 | 184 | 185 | 186 | 187 | 188 | 189 | 190 | 191 | 192 |
|---|---|---|---|---|---|---|---|---|---|---|---|
| Active Ingredient(s): | | | | | | | | | | | |
| D-Allethrin | 0 | 0 | 0 | 0 | 0 | 0 | 0 | 0 | 0 | 0 | 0 |
| Tetramethrin | 0 | 0 | 0 | 0 | 0 | 0 | 0 | 0 | 0 | 0 | 0 |
| Permethrin | 0.15 | 0.15 | 0.15 | 0.15 | 0.15 | 0.15 | 0.15 | 0.15 | 0.15 | 0.15 | 0.15 |
| Piperonyl Butoxide | 0 | 0 | 0 | 0 | 0 | 0 | 0 | 0 | 0 | 0 | 0 |
| Lactam(s): | | | | | | | | | | | |
| N-Methylpyrrolidone | 0 | 0 | 0 | 0 | 0 | 0 | 0 | 0 | 0 | 0 | 1.35 |
| N-Ethylpyrrolidone | 0 | 0 | 0 | 0 | 0 | 0 | 0 | 0 | 0 | 0 | 0 |
| N-Butylpyrrolidone | 1.35 | 1.35 | 1.35 | 1.35 | 1.35 | 1.35 | 1.35 | 1.35 | 1.35 | 1.35 | 0 |
| N-Dodecylpyrrolidone | 0 | 0 | 0 | 0.6 | 0 | 0 | 0 | 0.6 | 0 | 0 | 0.4 |
| N-octylpyrrolidone | 0 | 0 | 0.6 | 0 | 0 | 0 | 0.6 | 0 | 0 | 0 | 0 |
| Isooctylpyrrolidone | 0.4 | 0 | 0 | 0 | 0.6 | 0 | 0 | 0 | 0.6 | 0 | 0 |
| Tallowpyrrolidone | 0 | 0.4 | 0 | 0 | 0 | 0.6 | 0 | 0 | 0 | 0.6 | 0 |
| Surfactant(s): | | | | | | | | | | | |
| Igepal CO 630 | 1.2 | 1.2 | 1.8 | 1.8 | 1.8 | 1.8 | 1.8 | 1.8 | 1.8 | 1.8 | 1.2 |
| Gafac RE 610 | 0.4 | 0.4 | 0.6 | 0.6 | 0.6 | 0.6 | 0.6 | 0.6 | 0.6 | 0.6 | 0.4 |
| *diluted to 100% with | h | h | d | d | d | d | h | h | h | h | d |
| Total Surfactants | 1.6 | 1.6 | 2.4 | 2.4 | 2.4 | 2.4 | 2.4 | 2.4 | 2.4 | 2.4 | 1.6 |
| Stability: | | | | | | | | | | | |
| Time, observation at ambient conditions | | | | | | | | | | | |
| 0 time | clear | cloudy | clear | cloudy | clear | cloudy | clear | cloudy | clear | cloudy | cloudy |
| 1 day | clear | cloudy | clear | cloudy | clear | cloudy | clear | cloudy | clear | cloudy | |
| 2 days | | | | | | | | | | | |
| 4 days | clear | pcpt | clear | pcpt | clear | pcpt | clear | cloudy | clear | cloudy | cloudy |
| 6 days | | | | | | | | | | | cloudy |
| 2 weeks | | | | | | | | | | | |
| 4 weeks | | | | | | | | | | | |
| 6 weeks | | | | | | | | | | | cloudy |
| 2 months | | | | | | | | | | | cloudy |
| 3 months | clear | pcpt | clear | pcpt | clear | pcpt | clear | cloudy | clear | cloudy | |
| 6 months | | | | | | | | | | | |

| Run No. | 193 | 194 | 195 | 196 | 197 | 198 | 199 | 200 | 201 | 202 | 203 |
|---|---|---|---|---|---|---|---|---|---|---|---|
| Active Ingredient(s): | | | | | | | | | | | |
| D-Allethrin | 0 | 0 | 0 | 0 | 0 | 0 | 0 | 0 | 0 | 0 | 0 |
| Tetramethrin | 0 | 0 | 0 | 0 | 0 | 0 | 0 | 0 | 0 | 0 | 0 |

TABLE 6-continued

Microemulsion Composition for Permethrin with Mixed Alkyl Pyrrolidones (Percent by weight) and Stability

| | | | | | | | | | | | |
|---|---|---|---|---|---|---|---|---|---|---|---|
| Permethrin | 0.15 | 0.15 | 0.15 | 0.15 | 0.15 | 0.15 | 0.15 | 0.15 | 0.15 | 0.15 | 0.15 |
| Piperonyl Butoxide | 0 | 0 | 0 | 0 | 0 | 0 | 0 | 0 | 0 | 0 | 0 |
| Lactam(s): | | | | | | | | | | | |
| N-Methylpyrrolidone | 1.35 | 1.35 | 1.35 | 1.35 | 1.35 | 1.35 | 1.35 | 1.35 | 1.35 | 1.35 | 1.35 |
| N-Ethylpyrrolidone | 0 | 0 | 0 | 0 | 0 | 0 | 0 | 0 | 0 | 0 | 0 |
| N-Butylpyrrolidone | 0 | 0 | 0 | 0 | 0 | 0 | 0 | 0 | 0 | 0 | 0 |
| N-Dodecylpyrrolidone | 0.4 | 0.6 | 0.6 | 0 | 0 | 0 | 0 | 0 | 0 | 0 | 0 |
| N-Octylpyrrolidone | 0 | 0 | 0 | 0 | 0 | 0 | 0 | 0 | 0 | 0 | 0 |
| Isooctylpyrrolidone | 0 | 0 | 0 | 0.4 | 0.4 | 0.6 | 0.6 | 0 | 0 | 0 | 0 |
| Tallowpyrrolidone | 0 | 0 | 0 | 0 | 0 | 0 | 0 | 0.4 | 0.4 | 0.6 | 0.6 |
| Surfactant(s): | | | | | | | | | | | |
| Igepal CO 630 | 1.2 | 1.8 | 1.8 | 1.2 | 1.2 | 1.8 | 1.8 | 1.2 | 1.2 | 1.8 | 1.8 |
| Gafac RE 610 | 0.4 | 0.6 | 0.6 | 0.4 | 0.4 | 0.6 | 0.6 | 0.4 | 0.4 | 0.6 | 0.6 |
| *diluted to 100% with | h | d | h | d | h | d | h | d | h | d | h |
| Total Surfactants | 1.6 | 2.4 | 2.4 | 1.6 | 1.6 | 2.4 | 2.4 | 1.6 | 1.6 | 2.4 | 2.4 |
| Stability: | | | | | | | | | | | |
| Time, observation at ambient conditions | | | | | | | | | | | |
| 0 time | cloudy | cloudy | cloudy | cloudy | clear | clear | clear | cloudy | cloudy | cloudy | cloudy |
| 1 day | | | | | | | | | | | |
| 2 days | | | | | | | | | | | |
| 4 days | cloudy | cloudy | cloudy | clear | clear | clear | clear | cloudy | cloudy | cloudy | cloudy |
| 6 days | cloudy | cloudy | cloudy | | | | | cloudy | cloudy | cloudy | cloudy |
| 2 weeks | | | | | | | | | | | |
| 4 weeks | | | | | | | | | | | |
| 6 weeks | cloudy | cloudy | cloudy | clear | clear | clear | clear | cloudy | cloudy | cloudy | cloudy |
| 2 months | cloudy | cloudy | cloudy | clear | clear | | | cloudy | cloudy | cloudy | cloudy |
| 3 months | | | | | | | | | | | |
| 6 months | | | | | | | | | | | |

*h, means 342 ppm standard hard water; d, means deionized water.

TABLE 7

Microemulsion Composition for Hydramethylnon (Percent by weight) and Stability

| Run No. | 204 | 205 | 206 | 207 |
|---|---|---|---|---|
| Active Ingredient(s): | | | | |
| Hydramethylnon | 0.1 | 0.5 | 0.1 | 0.1 |
| Tetramethrin | 0 | 0 | 0 | 0 |
| Permethrine | 0 | 0 | 0 | 0 |
| Piperonyl Butoxide | 0 | 0 | 0 | 0 |
| Lactam(s): | | | | |
| N-Methylpyrrolidone | 0 | 0 | 0 | 5 |
| N-Ethylpyrrolidone | 0 | 0 | 0 | 0 |
| N-Butylpyrrolidone | 0 | 0 | 0 | 0 |
| N-Dodecylpyrrolidone | 0 | 0 | 0 | 0 |
| N-Octylpyrrolidone | 5 | 5 | 0 | 0 |
| Tallowpyrrolidone | 0 | 0 | 0 | 0 |
| Surfactant(s): | | | | |
| Igepal CO 630 | 0 | 0 | 0 | 0 |
| Gafac RE 610 | 0 | 0 | 0 | 0 |
| Sodium Dodecyl Sulfate | 2 | 2 | 2 | 2 |
| *diluted to 100% with | d | d | d | d |
| Total Surfactants | 2 | 2 | 2 | 2 |
| Stability: | | | | |
| Time, observation at ambient conditions | | | | |
| 0 time | clear | cloudy | pcpt | clear |
| 1 hour | clear | cloudy pcpt | pcpt | clear |
| 2 hours | clear | cloudy pcpt | pcpt | cloudy |
| 4 hour | clear | | | |
| 16 hours | cloudy | cloudy pcpt | pcpt | |
| 24 hours | cloudy | | | |

*h, means 342 ppm standard hard water; d, means deionized water.

TABLE 8

Microemulsion Composition for Carbaryl (Percent by weight) and Stability

| Run No. | 208 | 209 | 210 | 211 | 212 | 213 | 214 |
|---|---|---|---|---|---|---|---|
| Active Ingredient(s): | | | | | | | |
| Carbaryl | 0.1 | 0.5 | 0.1 | 0.1 | 0.3 | 0.3 | 0.3 |
| Tetramethrin | 0 | 0 | 0 | 0 | 0 | 0 | 0 |
| Permethrine | 0 | 0 | 0 | 0 | 0 | 0 | 0 |
| Piperonyl Butoxide | 0 | 0 | 0 | 0 | 0 | 0 | 0 |
| Lactam(s): | | | | | | | |
| N-Methylpyrrolidone | 0 | 0 | 0 | 5 | 0 | 5 | 0 |
| N-Ethylpyrrolidone | 0 | 0 | 0 | 0 | 0 | 0 | 0 |
| N-Butylpyrrolidone | 0 | 0 | 0 | 0 | 0 | 0 | 0 |
| N-Dodecylpyrrolidone | 0 | 0 | 0 | 0 | 0 | 0 | 0 |
| N-Octylpyrrolidone | 5 | 5 | 0 | 0 | 5 | 0 | 0 |
| Tallowpyrrolidone | 0 | 0 | 0 | 0 | 0 | 0 | 0 |
| Surfactant(s): | | | | | | | |
| Igepal CO 630 | 0 | 0 | 0 | 0 | 0 | 0 | 0 |
| Gafac RE 610 | 0 | 0 | 0 | 0 | 0 | 0 | 0 |
| Sodium Dodecyl Sulfate | 2 | 2 | 2 | 2 | 2 | 2 | 20 |
| *diluted to 100% with | d | d | d | d | d | d | d |
| Total Surfactants | 2 | 2 | 2 | 2 | 2 | 2 | 2 |
| Stability: | | | | | | | |
| Time, observation at | | | | | | | |

TABLE 8-continued

| Run No. | Microemulsion Composition for Carbaryl (Percent by weight) and Stability | | | | | | |
|---|---|---|---|---|---|---|---|
| | 208 | 209 | 210 | 211 | 212 | 213 | 214 |
| ambient conditions | | | | | | | |
| 0 time | clear | clear | pcpt | clear | clear | clear | pcpt |
| 1 day | clear | pcpt | pcpt | clear | clear | pcpt | pcpt |
| 2 days | clear | pcpt | pcpt | clear | clear | pcpt | pcpt |
| 4 days | clear | pcpt | pcpt | clear | clear | pcpt* | pcpt* |
| 6 days | clear & colorless | | | clear colored red | clear | | |
| 2 weeks | clear & colorless | | | | clear & colorless | | |
| 4 weeks | | | | | | | |
| 6 weeks | | | | | | | |
| 2 months | | | | | | | |
| 3 months | | | | | | | |
| 6 months | | | | | | | |
| pH at 0 time | 8.0 | | | 7.7 | 8.4 | 8.7 | 8.6 |

*supernatant colored

*h, means 342 ppm standard hard water; d, means deionized water.

What is claimed is:

1. A clear, efficacious, aqueous microemulsion of an agriculturally active ingredient wherein the dispersed phase consists of small droplets with diameters in the range of about 10 to 100 millimicrons which is stable at or below room temperature for an extended period of time, consisting essentially of:
   (a) about 0.005-2% by weight of a water-insoluble agriculturally active ingredient,
   (b) about 0.01-15% by weight of a surfactant,
   (c) about 0.01-15% by weight of a $C_1$-$C_4$ alkyl pyrrolidone, or a $C_6$-$C_{18}$ alkyl pyrrolidone, or both, and
   (d) at least about 80% by weight water wherein the agriculturally active ingredient optionally contains a synergist.

2. A clear, efficacious, aqueous microemulsion according to claim 1 wherein said $C_1$-$C_4$ alkyl pyrrolidone is N-methyl pyrrolidone, and said $C_6$-$C_{18}$ alkyl pyrrolidone is octyl pyrrolidone, iso-octyl pyrrolidone or N-dodecyl pyrrolidone, or mixtures thereof.

3. A clear, efficacious, aqueous microemulsion according to claim 1 including both a $C_1$-$C_4$ alkyl pyrrolidone and a $C_6$-$C_{18}$ alkyl pyrrolidone therein.

4. A clear, efficacious, aqueous microemulsion according to claim 1 including a synergist for the agriculturally active ingredient.

5. An aqueous microemulsion according to claim 1 wherein (a) is 0.01-0.5%, (b) is 0.03-5%, and (c) is 0.03-10%.

6. A microemulsion concentrate for forming a clear, efficacious aqueous microemulsion upon dilution with water, consisting essentially of:
   (a') about 0.5-25% by weight of a water-insoluble agriculturally active ingredient;
   (b') about 0.2-80% by weight of a surfactant, wherein the ratio of (a'):(b') is 1:0.3 to 1:10; and
   (c') a $C_1$-$C_4$ alkyl pyrrolidone, or a $C_6$-$C_{18}$ alkyl pyrrolidone, or both, wherein the agriculturally active ingredient optionally contains a synergist.

7. A microemulsion concentrate according to claim 6 wherein said $C_1$-$C_4$ alkyl pyrrolidone is N-methyl pyrrolidone, and said $C_6$-$C_{18}$ alkyl pyrrolidone is octyl pyrrolidone, iso-octyl pyrrolidone or N-dodecyl pyrrolidone, or mixtures thereof.

8. A microemulsion concentrate according to claim 6 including both a $C_1$-$C_4$ alkyl pyrrolidone and a $C_6$-$C_{18}$ alkyl pyrrolidone therein.

9. A microemulsion concentrate according to claim 6 including a synergist for the agriculturally active ingredient.

10. A microemulsion concentrate according to claim 6 wherein (a') is 5-25%, (b') is 5-60%, and the ratio of (a'):(b') is 1:0.5-1:8.

11. A microemulsion concentrate according to claim 6 wherein (a') is 10-25%, (b') is 10-50%, and the ratio of (a'):(b') is 1:1-1:6.

* * * * *